(12) United States Patent
Zhang et al.

(10) Patent No.: US 6,548,266 B1
(45) Date of Patent: Apr. 15, 2003

(54) ASSAY FOR DETECTING THE ENZYMATIC ACTIVITY OF A PHOSPHORYLATION ENZYME USING ENHANCED SIGNAL GENERATION

(75) Inventors: Zaihui Zhang, Richmond (CA); Jasbinder Sanghera, Vancouver (CA); Shisen Wang, Coquitlam (CA)

(73) Assignee: Kinetek Pharmaceuticals, Inc., Vancouver (CA)

( * ) Notice: Subject to any disclaimer, the term of this patent is extended or adjusted under 35 U.S.C. 154(b) by 0 days.

(21) Appl. No.: 10/009,120
(22) PCT Filed: May 26, 2000
(86) PCT No.: PCT/CA00/00622
§ 371 (c)(1),
(2), (4) Date: May 21, 2002
(87) PCT Pub. No.: WO00/75667
PCT Pub. Date: Dec. 14, 2000

Related U.S. Application Data

(60) Provisional application No. 60/137,670, filed on Jun. 4, 1999.

(51) Int. Cl.[7] .............................. C12Q 1/48; C12Q 1/42; C12Q 1/37; C12Q 1/00
(52) U.S. Cl. .............................. 435/15; 435/21; 435/23; 435/24; 435/4; 435/174; 435/183; 435/7.1
(58) Field of Search .............................. 435/15, 21, 23, 435/24, 4, 174, 183, 7.1

(56) References Cited

U.S. PATENT DOCUMENTS

| | | | |
|---|---|---|---|
| 5,759,787 A | 6/1998 | Strulovici | 435/7.4 |
| 5,763,198 A | 6/1998 | Hirth et al. | 435/7.21 |
| 6,054,280 A | * 4/2000 | Lemmon et al. | 435/7.1 |

OTHER PUBLICATIONS

Angeles, Thelma S. et al., *Enzyme–Linked Immunosorbent Assay for TRKA Tyrosine Kinase Activity*, Analytical Biochemistry, (Sep. 12, 2995), V. 236, pp. 49–55 Article No. 0130, Academic Press, Inc.

Forrer, Patrik et al., *Enzyme–Linked Immunosorbent Assay for Measurement of JNK, ERK, and P38 Kinase Activities*, Biol. Chem., (1998), V. 379, pp. 1101–1111, Walter de Gruyter–Berlin–New York.

Kameshita, Isamu et al., *Detection of Protein Kinase Activities Toward Oligopeptides in Sodium Dodecyl Sulfate–Polyacrylamide Gel*[1], Analytical Biochemistry, (Nov. 13, 1995), V. 237, pp. 198–203, Academic Press, Inc.

Kameshita, Isamu et al., *A New Peptide Conjugate as a Highly Specific Substrate for Map Kinase*[1], J. Biochem., (Feb. 19, 1997), V. 122, pp. 168–172.

Williams, Richard T. et. al., *Identification Assay and Purification of a CDC2–Activating Threonine–161 Protein Kinase from Human Cells*, Archives of Biochemistry and Biophysics, (Jun. 21, 1994), V. 314, pp. 99–106, No. 1, Academic Press, Inc.

Woodgett, James Robert et al., *Use of Peptide Substrates for Affinity Purification of Protein–Serine Kinases*, Analytical Biochemistry, (Feb. 9, 1989), V. 180, pp. 237–241, Academic Press, Inc.

* cited by examiner

Primary Examiner—Louise N. Leary
(74) Attorney, Agent, or Firm—Pamela J. Sherwood; Bozicevic, Field & Francis LLP

(57) ABSTRACT

An assay system is provided for detecting the enzymatic activity of a phosphorylation enzyme. The enzyme may be a phosphatase or protein kinase. The substrate for the enzyme is immobilized on a solid support via covalent or non-covalent binding through a signal enhancing polymer. The immobilized substrate provides an enhanced signal to background ratio when compared to a substrate in solution. The methods are easily adapted to high throughput screening systems.

25 Claims, 2 Drawing Sheets

Octopus style

Tree branch style

Ball core style

Figure 1. Dendrimers terminating in primary amine groups.
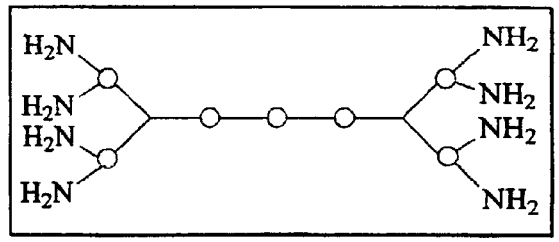
Octopus style
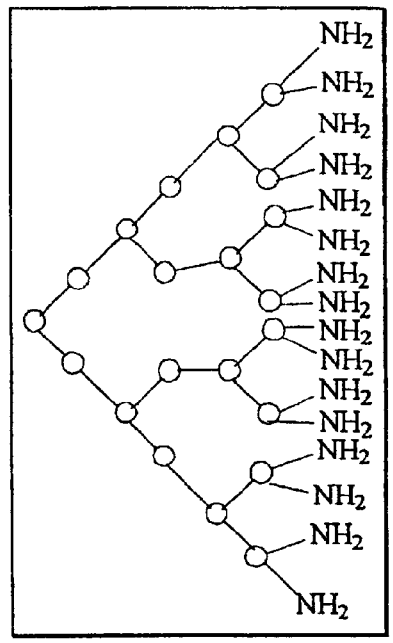
Tree branch style
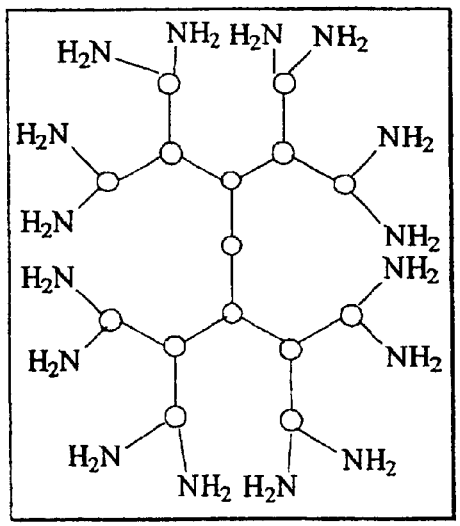
Ball core style

Figure 2. Phosphorylation activity of substrate conjugates as a function of SEK1-CT concentration.
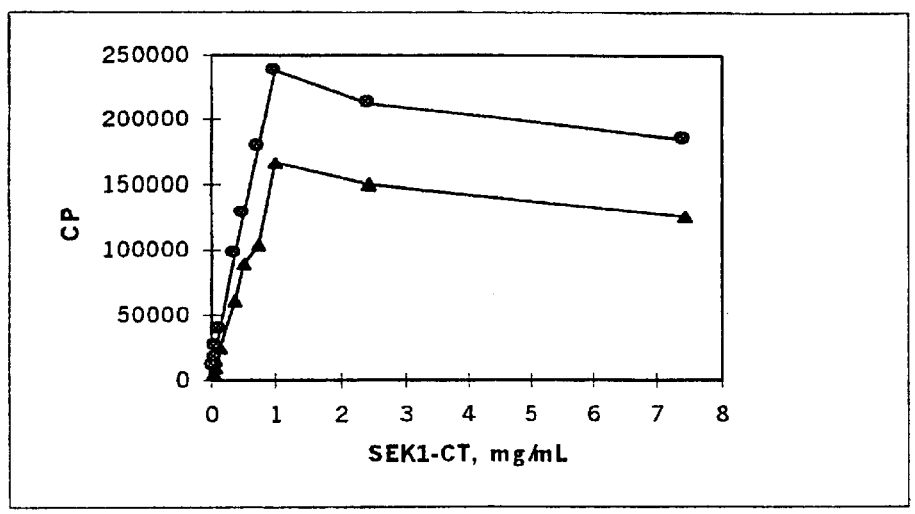
(● the polylysine-peptide conjugate *via* the linker SMCC, ▲ the conjugate *via* the linker GMBS.)

ASSAY FOR DETECTING THE ENZYMATIC ACTIVITY OF A PHOSPHORYLATION ENZYME USING ENHANCED SIGNAL GENERATION

This application is a 371 National Phase filing of PCT/CA00/00622 filed May 26, 2000 which claims benefit of Provisional Application 60/137,670 filed Jun. 4, 1999.

Multicellular organisms must coordinate the functions of various cells and tissues. Cell-to-cell communication usually occurs through secretion of molecules by one cell, which molecules then bind to receptors on another cell. Phosphorylation of proteins is a post-translational mechanism used by cells to selectively transmit regulatory signals from the receptors outside of the target cell into the nucleus. The molecules mediating these biochemical reactions are predominantly phosphorylation enzymes, a group that includes protein kinases, which catalyze the addition of phosphate; and protein phosphatases, which catalyze the removal of phosphate. These phosphorylation enzymes are defined by the substrate upon which they act and by their apparent function. Substrate specificity is determined by the enzyme interaction with key amino acid sequences at certain portions of the substrate protein.

Secondary signal transduction molecules generated by protein kinases or protein phosphatases lead to a 'cascade' of signaling which, in turn, regulates numerous cell functions including cell division, differentiation, transformation and death. Inhibition of specific protein kinases and phosphatases provides a means of intervening in these signaling pathways. Defects in signaling mediated by phosphorylation enzymes are associated with a variety of pathological or clinical conditions, including cancer, diabetes, autoimmune and immunodeficiency diseases, and neural disorders. Assays for specific protein kinase or phosphatase inhibitors enable the discovery of therapeutic agents for the treatment of conditions characterized by defects in protein phosphorylation.

Assays currently used for screening drugs and ligands that act on phosphorylation enzymes, in general, involve exposing whole cells or their constituents to a test substance, and measuring either phenotypic changes in the cell culture, or biochemically analyzing cell extracts to assess the levels and identities of phosphorylated proteins. Large numbers of natural and synthetic compounds are typically screened before a potential therapeutic agent is found. The screening steps are preferably performed by a robot to incorporate high speed with relative consistency. "High throughput screening" is a term given to semi-automated procedures that assay large numbers of samples at a time. Cell-free assays offer enhanced specificity and higher throughput over whole cell assays.

Assays are typically conducted in multiwell polystyrene plates. Standard microtiter plates offer small volumes as well as a large number of wells which can be assayed simultaneously. One drawback to the assays for kinase and phosphatase inhibitors is the difficulty in obtaining a definitive signal from the wells. The target enzymes are in many cases very hard to isolate and only small amounts are available. Subsequently, a very important target may be limited as a screening tool due to its scarcity. A two-plate screening procedure, in which the inhibition of a target phosphorylation enzyme is measured over a range of concentrations, overcomes some of these limitations, however, disadvantages associated with this procedure include the cost of using two plates per assay, transfer inefficiency and limited throughput due to the requirement for manual washing. Substrate immobilization on the surface of a microtiter plate removes the latter limitation and increases assay throughput, however, limited binding capacity on the plate surface, relatively low substrate activity and steric hindrance can make it difficult to achieve a high signal output.

Further development of techniques for rapidly screening large numbers of variously-reactive phosphorylation substrates and inhibitors would be of great benefit in drug discovery.

RELEVANT LITERATURE

U.S. Pat. No. 5,759,787 describes the use of a chemiluminescent protein kinase assay using biotinylated substrate peptides captured on a streptavidin coated microtiter plate, and monoclonal antibodies to detect their phosphorylation. U.S. Pat. No. 5,763,198 describes a high-throughput screening assay using antiphosphate antibodies bound to plates to bind phosphorylated proteins. Forrer et al. (1998) *Biol Chem* 379:1101–1111 disclose an enzyme-linked immunosorbent assay (ELISA) for measurement of the enzyme activity of the MAP kinases that involves immobilization of the respective kinase substrates on microtiter plates. An ELISA-based assay to measure trkA tyrosine kinase activity using a GST-fusion substrate immobilized on a microtiter plate is described by Angeles, et al. (1996) *Anal Biochem* 236:49–55. In-gel detection of protein kinase activities toward oligopeptides is disclosed in Kameshita et al. (1996) *Anal Biochem* 237:198–203.

Kameshita et al. (1997) *J Biochem* 122:168–172 describe a peptide conjugate as a highly specific substrate for MAP kinase.

SUMMARY OF THE INVENTION

Improved methods are provided for assaying compounds that modulate phosphorylation. The methods of the invention find particular use in high-throughput screening systems, gel assays and affinity chromatography. The substrate for an enzyme is immobilized by covalently linking it to a polymer and attaching the modified substrate to the surface of a solid support, which may be a plate, column resin, etc. The resulting increased enzyme-substrate contact leads to enhanced phosphorylation and increased sensitivity in detection. In one embodiment of the invention, a simplified and fully automated one-plate assay procedure is provided. The assay involves addition of the phosphorylation reaction mixture containing the enzyme and radiolabelled phosphate to the immobilized substrate and measurement of phosphorylation by scintillation counting.

In another embodiment of the invention, the modified substrate is phosphorylated and retained in a gel matrix, and phosphorylation is measured by autoradiography. In yet another embodiment of the invention, the modifed substrate is immobilized on beads to form an enzyme affinity matrix. The subject methods are useful for the rapid screening of inhibitors of phosphorylation, which may lead to the discovery of potential therapeutic agents.

BRIEF DESCRIPTION OF THE DRAWINGS

FIG. 1. Schematic representation of dendrimers terminating in primary amine groups.

FIG. 2. Graphical representation of phosphorylation activity of substrate conjugates as a function of SEK1-CT concentration.

DESCRIPTION OF THE SPECIFIC EMBODIMENTS

The subject methods provide a means for the detection of biologically active modulators of phosphorylation. The methods of the invention find particular use in high-throughput screening systems. The substrate for a phosphorylation enzyme is immobilized on a support by covalent linkage to a polymer that is bound on the surface of the support. The resulting increased enzyme-substrate contact leads to enhanced phosphorylation and increased sensitivity. A one-plate assay procedure is provided, and may be used in the identification of compounds that interfere with phosphorylation.

Advantages of the invention include higher throughput for high-throughput screening systems, reduced cost, efficient use of robotic systems, and increased level of signal to background noise. The invention also provides a means to carry out substrate immobilization and the phosphorylation simultaneously, offering added efficiency.

Enzyme kinetics models predict that physically constraining the substrate by immobilization would diminish the enzymatic activity towards the substrate, however it has been found that immobilization of the peptide substrate on a solid support, in accordance with the subject methods, increases enzyme-substrate contact and, thus, enhances phosphorylation. Constraining the peptide on a solid support also appears to mimic the presentation of the protein substrate to the enzyme.

DEFINITIONS

It is to be understood that this invention is not limited to the particular methodology, protocols and reagents described, as such may vary. It is also to be understood that the terminology used herein is for the purpose of describing particular embodiments only, and is not intended to limit the scope of the present invention which will be limited only by the appended claims.

It must be noted that, as used herein and in the appended claims, the singular forms "a", "and", and "the" include plural referents unless the context clearly dictates otherwise. Thus, for example, reference to "a compound" includes a plurality of such compounds and reference to "the enzyme" includes reference to one or more enzymes and equivalents thereof known to those skilled in the art, and so forth. All technical and scientific terms used herein have the same meaning as commonly understood to one of ordinary skill in the art to which this invention belongs unless clearly indicated otherwise. Although any methods, devices and materials similar or equivalent to those described herein can be used in the practice or testing of the invention, the preferred methods, devices and materials are now described.

Substrate. as used herein refers to any protein or peptide that is acted on by a kinase or phosphatase, such that it is either phosphorylated or dephosphorylated, particularly on serine, threonine or tyrosine residues within a phosphorylation site motif. A recent compilation of phosphorylation sites can be found in Pinna et al. (1996) *Biochim Biophys Acta* 1314:191–225. In one embodiment of the invention, the substrate is a peptide comprising one tyrosine in a phosphorylation site motif.

In the methods of the present invention, a substrate is conjugated to a signal enhancing polymeric carrier. Such a conjugation influences the availability and specificity of a substrate for an enzyme. The polymer may also alter or improve properties such as solubility, stability and membrane permeability.

Signal enhancing polymers are polymeric molecules that generally comprise amine groups, and may include dendrimers containing amine groups, such as lysine-based dendritic macromolecules. Examples include poly-amino acids containing amine groups, such as polylysine, polyarginine, poly-(lysine, alanine) copolymers, polyhistidine, and chitin or chitosan. Preferred polymeric carriers are polylysine or lysine-containing polymers. The structure and topology may be variable, as shown in FIG. 1. The molecular weight of the polymer may range from about 400 to about 500,000 Daltons but is preferably about 30,000 to about 250,000 Daltons, and most preferably 30,000 to 70,000 Daltons.

In a preferred embodiment of the invention the substrate is a peptide that comprises at least one thiol group at the amino or carboxy terminus. Conjugation of the substrate to a poylmeric carrier is achieved by indirectly coupling thiol groups in the substrate with amine groups in the polymer.

Immobilization as used herein is intended to refer to attachment of a substrate to a support, which may be a planar surface, microsphere, matrix, or the like. A polystyrene surface is often used for immobilization, because polystyrene is hydrophobic and easily modified by radiation or chemical techniques. The polystyrene may be in a variety of forms, e.g. beads or microspheres, plates, capillaries, etc.

Polypeptides, proteins or other biomolecules are attached to the support via covalent or non-covalent mechanisms. Non-covalent immobilization consists of primarily hydrophobic interactions or hydrophobic-ionic interactions between the biomolecule and the unmodified or modified polystyrene surface. Covalent immobilization is accomplished by first modifying polystyrene to incorporate a functional group, such as an amine or carboxyl group, then coupling said functional group to a complementary functional group, such as an amine or sulfydryl, on the biomolecule.

Other matrices are also suitable for immobilization, e.g. sepharose or agarose. These polymers are easily modified to incorporate a reactive functional group, such as an amine or sulfhydryl group, for the covalent attachment of a substrate containing complementary functional groups. Conditions such as pH and temperature can influence immobilization.

Support refers to an insoluble support, e.g. microtiter plate, petri dish, microspheres, beads or particles as may be used in a column or "tea bag" configuration, etc. Physical properties of the support, such as size, shape and pigment (e.g., clear, opaque) can affect the performance of assays. The chemical properties of the solid support, such as hydrophobicity, reactivity, etc., are largely determined by the composition of the surface. In a specific embodiment of the invention, the solid support is a multiwell microtiter plate with a polystyrene surface.

Bifunctional linker. A chemical agent that contains two reactive groups used to conjugate or "crosslink" a phosphorylation enzyme substrate to a signal enhancing polymer. Heterobifunctional crosslinking agents often contain a succinimidyl ester and either a maleimide or an iodoacetamide. Useful bifunctional linkers include succinimidyl 4-(N-maleimidomethyl)-cyclohexane-1-carboxylate (SMCC), sulfosuccinimidyl 4-(N-maleimidomethyl)cyclohexane-1-carboxylate (sulfo-SMCC), succinimidyl 3-(2-pyridyldithio)propionate (SPDP), succinimidyl 4-maleimidobutyrate (GMBS), and succinimidyl 6-maleimidocaproate (EMCS).

Generally, bifunctional linkers are used in the invention to link thiol groups of the substrate to amine groups of the polymer. The polymer amine groups react with the succinimidyl ester portion of the linker to form an amide. The substrate thiol groups react with the maleimide or iodoacetamide of the modified polymer to form a stable thioether crosslink. The heteroconjugate thus formed has an optional hydrocarbon chain, or ring of 2 to 12 atoms in length between the substrate and the polymer in the preferred embodiment, which hydrocarbon may be substituted with heteroatoms, as known in the art.

Phosphorylation Assay. A procedure to determine phosphorylation activity of a phosphorylation enzyme on a substrate in vitro. The phosphorylation assay is conducted in a buffered solution containing the enzyme, the immobilized substrate and a detectably labeled source of phosphate. Enzymes of interest include serine/threonine and tyrosine kinases. These enzymes use the γ-phosphate of ATP or GTP to generate phosphate monoesters utilizing protein alcohol groups on serine or threonine, and/or protein phenolic groups (tyrosine) as phosphate group acceptors.

Enzyme concentrations ranging from at least about 50 $\mu$M to not more than about 1 mM are preferred, usually not more than about 500 $\mu$M, and more usually not more than about 250 $\mu$M. Substrate concentrations vary, but are usually at least about 10 $\mu$g/ml and not more than about 10 mg/ml, more usually at least about 100 $\mu$g/ml and not more than about 1 mg/ml. Exemplary is about 1 mg/ml in a volume of 5 $\mu$l. Radiolabeled phosphate is the preferred source of phosphate, in stock solutions of about 1–5 mM. Because most kinases have $K_m$ values for ATP in the range of about 10–150 $\mu$M, saturating concentrations of ATP are used to arrive at values of $K_m$ and $v_{max}$ for the substrates.

In a specific embodiment of the invention, the reaction mixture is incubated and the reaction terminated by spotting aliquots onto a phosphocellulose membrane. Both the phosphorylated and non-phosphorylated forms of the substrate bind to the membrane while ATP (unincorporated phosphate) is removed in the subsequent wash steps. The incorporation of radiolabelled phosphate into the substrate is determined by direct scintillation counting. Preferred substrates have a net positive charge for quantitative binding to phosphocellulose membranes.

In an alternative embodiment, the substrate is immobilized on beads. The assay is performed with the beads suspended in an appropriate buffer, and the unincorporated phosphate is removed by washing the beads and removing the supernatant. The incorporation of label is determined by counting of the labeled phosphate bound to the beads.

The assay is performed in any format that allows rapid preparation and processing of multiple reactions such as in, for example, 96-well microtiter plates. In preferred embodiments, stock solutions of the assay components as well as test agents are prepared manually and all subsequent pipetting, diluting, mixing, washing, incubating, sample readout and data collection is done using commercially available robotic pipetting equipment, automated work stations, and analytical instruments for detecting the signal generated by the assay.

The assay conditions will vary depending on the enzyme/substrate system. Optimization may be performed using conventional methods for each enzyme/substrate system.

Sensitivity. A qualitative measure of the ratio of the radioactivity of the phosphorylated substrate (signal) to the background radioactivity (noise), where a high signal-to-noise ratio denotes high sensitivity.

High-throughput Screening. A procedure whereby a large number of test compounds are assayed rapidly for their effect on phosphorylation. The methods described herein are amenable to automation, whereby hundreds of test compounds, such as those found in a combinatorial library, might be processed in a single day, or thousands in a single week.

Affinity Chromatography. Affinity chromatography is used as a method of separating and purifying protein kinases and phosphatases using the biochemical affinity of the enzyme for the peptide substrate. In the present invention, an improvement is provided by the use of substrates coupled to a support. The peptide substrates are coupled to a matrix or gel through the previously described linkers.

Preferably a microsphere or matrix is used as the support for affinity chromatography. Such supports are known in the art and commercially available, and include activated supports that can be coupled to the linker molecules. For example, Affi-Gel supports, based on agarose or polyacrylamide are low pressure gels suitable for most laboratory-scale purifications with a peristaltic pump or gravity flow elution. Affi-Prep supports, based on a pressure-stable macroporous polymer, are suitable for preparative and process scale applications.

The substrate coupled support is used to separate an enzyme that acts on the substrate from a complex mixture, e.g. a cell lysate, that may optionally be partially purified. The sample mixture is contacted with the substrate coupled support under conditions that allow binding of the substrate and cognate enzyme, but which minimize non-specific binding. Methods known in the art include columns, gels, capillaries, etc. The unbound compounds are washed free of the resin, and the bound proteins are then eluted in a suitable buffer.

METHODS OF SCREENING

The subject methods are used to assay for the activity of a phosphorylation enzyme, which may be a phosphatase or a protein kinase, in a reaction mix. In an alternative embodiment, the supports comprising bound substrate are used to separate the desired phosphorylation enzymes from a complex mixture. The sensitivity of conventional assays is improved by the immobilization of the enzyme substrate onto a solid support. Preferred is a covalent attachment of the substrate to amine-binding plates or strips, which may be accomplished by conjugation of the substrate to the polymer using a bifunctional linker containing a succinimidyl ester and a maleimide. Preferred substrates are peptides containing a thiol group at the carboxy terminus and a free amino terminus.

The reaction mix will typically comprise an agent that is a candidate for modulation of phosphorylation, acting to either inhibit or enhance the activity of a phosphatase or kinase enzyme. The methods are used to identify agents that modulate the activity of phosphorylation enzymes. Such agents are natural or synthetic compounds that cause an increase or decrease in substrate phosphorylation. The screening of modulating agents is useful in the discovery of therapeutic agents for the treatment of conditions characterized by defects in protein phosphorylation. Of particular interest are compounds that are active in inhibiting kinase proteins, i.e., there is a decrease in the phosphorylation of a specific substrate in the presence of the compound. Preferred inhibitors are specific, i.e., there is substantially more inhibition of the targeted kinase as compared to non-targeted kinase proteins.

In one embodiment of the invention the immobilized substrate is prepared as follows: a signal enhancing polymer is modified to contain a maleimide or iodoacetamide functional group, by reaction with a heterobifunctional crosslinking agent. The enzyme substrate then reacts with the maleimide or iodoacetamide group on the polymer to form a stable heteroconjugate. The signal enhancing polymer-substrate conjugate is then reacted covalently or non-covalently with functional groups on the surface of a support to complete the immobilization process.

In another embodiment of the invention the immobilized substrate is prepared by first covalently or non-covalently attaching the signal enhancing polymer to the surface of the support. The immobilized polymer is then modified using a heterobifunctional crosslinking agent to contain a maleimide or iodoacetamide functional group. The substrate reacts with the maleimide or iodoacetamide to form a stable heteroconjugate, thereby completing the immobilization process.

In a further embodiment of the invention the substrate is immobilized and phosphorylated simultaneously. The signal enhancing polymer is covalently or non-covalently attached to the surface of the support, then modified using a hetero-bifunctional crosslinking agent to contain a maleimide or iodoacetamide functional group. Both the substrate and the phosphorylation enzyme are added to the modified immobilized polymer. The substrate reacts with the maleimide or iodoacetamide to form a stable heteroconjugate, and with the phosphorylation enzyme. In a variation on this method, the substrate may be conjugated to the signal enhancing polymer and pre-incubated with the enzyme prior to the immobilization step.

The phosphorylation assay is typically performed in the presence of a candidate modulating agent that is a candidate for inhibiting or enhancing the phosphorylation reaction. The candidate modulating agent is incubated with the enzyme, the immobilized substrate and radiolabeled phosphate. The degree of modulation, e.g. inhibition or enhancement of phosphorylation, is determined by comparing the amount of radioactivity incorporated in the presence of the test compound (i.e., the sample activity) to the amount of radioactivity incorporated in the absence of the test compound (i.e., the baseline activity). The % change is expressed by the following formula:

% change=100−(sample activity/baseline activity*100)

and is usually expressed in conjunction with the test agent concentration.

For example, by using a range of inhibitor concentrations, the $IC_{50}$ of an inhibitor is estimated (i.e. the concentration at which enzymatic activity is reduced by 50%). The $IC_{50}$ of various compounds against a particular target enzyme can be compared, whereby a lower $IC_{50}$ indicates a more potent compound.

All publications mentioned herein are incorporated herein by reference for the purpose of describing and disclosing, for example, the methods and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention;

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g., amounts, temperature, concentrations, etc.) but some experimental errors and deviations should be allowed for. Unless otherwise indicated, parts are parts by weight, molecular weight is average molecular weight, and pressure is at or near atmospheric.

EXAMPLES

Materials and Methods

Corning Costar® 96-well microtiter plates and strips were purchased from Fisher Scientific. MultiScreen® phosphocellulose PH plates, 96-well format, were purchased from Millipore. NICK Columns prepacked with Sephadex® G-50F and γ-$^{32}$P-ATP (10 mCi/mL) were purchased from Pharmacia Biotech. Affi-Gel 10 affinity chromatography support was obtained from Bio-Rad Laboratories. Dithothreitol (DTT) and the following polyamino acids were purchased from Sigma-Aldrich: poly-L-lysine with molecular weights of 30,000–70,000, 70,000–150,000, 150,000–300,000 and >300,000; poly-L-arginine with molecular weights of 42,400 and 92,000; and poly-L-(lysine, alanine) copolymers (1:1, 1:3) with molecular weights of 40,000–50,000 and ~35,000, respectively. N,N-dimethyl formamide (DMF) (anhydrous or Glass distilled, Omnisolv) was purchased from VWR. SMCC, Sulfo-SMCC, GMBS and EMCS were obtained from Sigma-Aldrich and Pierce Chemicals. Reagents were used as received.

Enzymes described in the following examples are listed in Table 1. CDK1, PAK and PIM were grown in bacterial culture at Kinetek Pharmaceuticals. PIM was isolated as described by Palaty et al. (1997) *J Biol Chem* 272:10514–10521. PKA was isloated from bovine heart. PKB was expressed in insect cells. S6K was isolated according to Grove et al. (1991) *Mol Cell Bio* 11:5541–5550. Kinase stock solutions were prepared at concentrations of 1–10 mg/mL in 150 mM Tris-Cl (pH 7.5) containing 5 mg/mL BSA and 100 mM $MgCl_2$.

TABLE 1

Exemplary kinases

| SEQ ID NO: | Designation | Activity |
| --- | --- | --- |
| 1 | CDK1 | Cyclin-dependent kinase |
| 2 | ERK1 | Extracellularly regulated protein kinase |
| 3 | PAK | p21-activated kinase |
| 4 | PIM | |
| 5 | PKA | CAMP-dependent protein kinase |
| 6 | PKB | CAMP-dependent protein kinase |
| 7 | S6K | Ribosomal protein S6 kinase |

Substrates described in the following examples were custom synthesized and are listed in Table 2.

TABLE 2

Exemplary peptide substrates.

| SEQ ID NO: | Designation | Sequence |
| --- | --- | --- |
| 8 | CAPK-sub | CGRTGRRNSI |
| 9 | PKB-sub | CKRPRAASFAE |
| 10 | SEK1-CT | CKILDQMPATPSSPMYVD |
| 11 | S6K-sub | CKRRRLASLR |

The assay diluting buffer (ADB) was prepared by mixing 1.0 M β-glycerophosphate (1.25 mL), 1 M MOPS (1 mL), 0.25 M EGTA (1 mL), 0.1 M EDTA (1 mL), 1 M $MgCl_2$ (1 mL), 0.25 M DTT (50 μL) and 5 mM β-methyl aspartic acid (50 μL) and diluting the mixture with distilled water to a final volume of 50 mL. Aliquots (5 mL) were stored at −20° C.

The phosphorylation assay mixture typically comprised:

5 μL substrate or polymer-conjugated substrate,

10 μL enzyme, and

5–10 μL γ-$^{32}$P-ATP diluted to a total volume of 30 μL with ADB. Variations are noted.

KTr-A buffer: 20 mM Tris, pH 7.4, 20 mM sodium fluoride, 20 mM beta-glycerophosphate, 1 mM EDTA, 1 mM EGTA. KTr-B buffer: KTr-A with 0.8 M sodium chloride added.

Example 1

Conjugation of a Peptide Substrate to a Polymeric Carrier

A general procedure for peptide conjugation to polymeric carrier is described using polylysine and succinimidyl 4-(N-maleimidomethyl)-cyclohexane-1-carboxylate (SMCC).

Introduction of maleimide group to poly-L-Lysine. SMCC (1 mg) dissolved in 30 μL of anhydrous DMF was mixed with a solution of polylysine (MW 70,000–150,000, 1 mg) in 250 μL of PBS (pH 7.0). The cloudy mixture was stirred for one hour at 30° C. The white solid from the reaction mixture was separated by spinning at 10,000 rpm for 5 minutes using a table top centrifuge apparatus. The supernatant was then loaded onto a Sephadex® G-50F NICK Column equilibrated with 2.5×PBS (pH 6.0), and the purified maleimido-functionalized polylysine fraction (330 μL) was collected.

Conjugation of the peptide to poly-L-lysine. The maleimido-functionalized poly-L-lysine solution thus obtained was mixed with a solution containing 1 mg of the peptide to be immobilized in 750 μL of water. After the addition of 25 μL of 0.2 M EDTA solution, the reaction was set in a 4° C. refrigerator overnight. The reaction was terminated by the addition of ~0.9 mg DTT. The final solution with a concentration of 1 mg/mL of the conjugated substrate was assayed directly.

Example 2

Phosphorylation of the Polymer-conjugated Peptide Substrate by a Protein Kinase

The phosphorylation of the polymer-conjugated substrate was carried out in a solution containing 5 μL (~5 μg peptide) of the conjugated substrate, 10 μL of the indicated enzyme, 10 μL of ADB, and 5 μL of γ-$^{32}$P-ATP. After incubation at room temperature for 15 minutes, the reaction was stopped by spotting 10 μL of the sample solution on a phosphocellulose plate and washing with water, 1% phosphoric acid solution, water and ethanol. The radioactivity in each well was measured using a Trilux Microbeta 1450 liquid scintillation counter (Wallac). The results are summarized in Table 3.

TABLE 3

Phosphorylation activity of peptide substrates after conjugation to polymer.

| | Radioactivity (cpm) | | |
|---|---|---|---|
| Kinase/Substrate | Before Conjugation | After conjugation | Ratio |
| S6K/CAPK-sub | 10000 | 62500 | 6.25 |
| S6K/S6K-sub | 14000 | 39450 | 2.82 |
| PIM/CAPK-sub | 18000 | 41500 | 2.31 |
| ERK1/SEK1-CT | 2390 | 115400 | 48.28 |
| CDK1/CAPK-sub | 12500 | 47000 | 3.76 |
| PAK/CAPK-sub | 31050 | 66510 | 2.14 |
| PKA/CAPK-sub | 35680 | 39425 | 1.10 |
| PKB/PKB-sub | 54300 | 103900 | 1.91 |

Example 3

Linker Effect on the Phosphorylation Activity of the Conjugated Peptide Substrate Succinimidyl 4-(N-maleimidomethyl)-cyclohexane-1-carboxylate (SMCC), sulfosuccinimidyl 4-(N-maleimidomethyl)cyclohexane-1-carboxylate (sulfo-SMCC), succinimidyl 4-maleimidobutyrate (GMBS) and succinimidyl 6maleimidocaproate (EMCS) were used to conjugate SEK1-CT to poly-L-lysine (MW 70,000–15,000). Substrate phosphorylation was carried out using ERK1, as described in Example 2. The effect of the linker on the phosphorylation activity of a conjugated substrate is summarized in Table 4.

TABLE 4

Phosphorylation activity of SEK1-CT conjugated to polylysine using different linkers.

| Linker | Radioactivity (cpm) |
|---|---|
| GMBS | 166500 |
| SMCC | 237500 |
| EMCS | 174850 |
| Sulfo-SMCC | 168600 |

Example 4

Polymer Effect on the Phosphorylation Activity of the Polymer-conjugated Peptide Substrate The following polymers were used to study the effect of polymeric carriers on the phosphorylation activity of a peptide substrate: polylysine, polyarginine, poly(lys, ala) copolymer with two different blending ratios (1:1 and 3:1), polyhistidine, and chitosan. SEK1-CT was conjugated to polymeric carriers, as described in Example 1. Phosphorylation was carried out using ERK1, as described in Example 2. Due to the solubility of chitosan under the assay conditions, no satisfactory results were obtained from chitosan. Polyhistidine showed marginal enhancing effect on the substrate activity. Polyarginine showed certain enhancement, however, the degree of enhancement on substrate activity was not as high as that shown by polylysine. Polylysine and poly(lys, ala) (3:1 and 1:1 ratio) copolymers demonstrated similar enhancing effects on the substrate activity. Among these polymers investigated, polylysine and poly(lys, ala) copolymer yielded the highest enhancing effect on the substrate activity. The results are summarized in Table 5.

TABLE 5

Polymer effect on the phosphorylation of SEK1-CT by ERK1

| Polymer | Radioactivity (cpm) |
|---|---|
| Polyarginine | 91431 |
| poly(lys,ala) 3:1 | 308908 |
| poly(lys,ala) 3:1 | 179356 |
| Polylysine | 211234 |

Example 5

The Effect of Polymer Molecular Weight on the Phosphorylation Activity of the Polymer-conjugated Peptide Substrate Four samples of SEK1-CT conjugated to polylysines with different molecular weights were prepared, as described in Example 1. The phosphorylation activity of the polymer-conjugated substrates towards ERK1 was compared and the results are shown in Table 6. The activity of polymer-conjugated SEK1-CT was highest for the polylysine with MW 30,000–70,000. No significant difference in the substrate activity was observed for polylysine with a MW>70,000.

TABLE 6

Phosphorylation activity of polylysine conjugated SEK1-CT.

| Polylysine MW | Radioactivity (cpm) |
|---|---|
| 30,000–70,000 | 170810 |
| 70,000–150,000 | 105450 |
| 150,000–300,000 | 98910 |
| 300,000 | 114420 |

Example 6

Effect of Conjugation Time Between the Peptide Substrate and the Linker

The effect of conjugation time between the peptide substrate and the linker-functionalized polymer on substrate activity was determined using SEK1-CT and polylysine (MW 70,000–15,000) functionalized using SMCC. The results are summarized in Table 7.

TABLE 7

Effect of conjugation time on the phosphorylation activity of the polylysine SEK1-CT.

| Time (hours) | Radioactivity (cpm) | Time (hours) | Radioactivity (cpm) |
|---|---|---|---|
| 0.25 | 174000 | 5.75 | 185630 |
| 0.75 | 201940 | 21 | 155860 |
| 1.75 | 206770 | 24 | 180790 |
| 3.75 | 197520 | 29 | 190395 |

No significant difference in activity was observed among the time periods studied. The results indicate a very efficient and fast conjugation between the thiol group on the substrate and the maleimide group on the linker.

Example 7

Effect of Substrate Concentrations

Substrate concentrations were varied using different molar ratios of SEK1-CT to SMCC-functionalized polylysine (MW 70,000–15,000). The molar ratio of the substrate to the linker varied from 1:1 to 1:250, corresponding to a loaded concentration of SEK1-CT from 7.4 to 0.03 mg/mL. Samples of polylysine conjugated to SEK1-CT were prepared in the specified molar ratios using either SMCC or GMBS as the linker, as described in Example 1. The conjugates were phosphorylated by ERK1, and the results are illustrated in FIG. 2. In both cases, the substrate activity increased with the substrate concentration. Substrate activity reached a maximum at 1 mg/mL.

Example 8

Immobilization of a Polylysine-conjugated Substrate on Covalent, Amine-binding Plates The polylysine-conjugated peptide substrate was diluted with a PBS buffer (pH 7.4) to a concentration of 0.1 mg/mL. Then 100 μL of the diluted solution was placed into each well of the covalent, amine-binding plate. The plate was incubated at room temperature for one hour and then washed with the PBS buffer three times and distilled water once. The substrate-immobilized plate was then phosphorylated as using standard assay conditions: 10 μL of the indicated enzyme, 15 μL of ADB and 5 μL of γ-$^{32}$P-ATP at room temperature for 15 minutes. After phosphorylation, the plate was rinsed sequentially with water, 1% phosphoric acid solution, water, and ethanol. The radioactivity in each well was determined using a Trilux Microbeta liquid scintillation counter. Two polylysine-conjugated substrates were immobilized on the covalent, amine-binding plates and phosphorylation of these immobilized polylysine-conjugated substrates was carried out. The results are summarized in Table 8. Both systems yielded reasonably high signals and the background signals on these plates were less than 500 cpm.

TABLE 8

Phosphorylation activity of substrates immobilized on covalent, amine-binding plates.

| | Radioactivity (cpm) | |
|---|---|---|
| Kinase/Substrate | Free substrate | Conjugated substrate |
| ERK1/SEK1-CT-SMCC-polylysine | <500 | 15624 |
| ERK1/SEK1-CT-SMCC-polylysine | N/A | 38300[a] |
| PIM/CAPK-sub-SMCC-polylysine | ≦300 | 5820 |

[a]Simultaneous immobilization and phosphorylation by ERK1.

Example 9

Immobilization of a Polylysine-conjugated Substrate on Covalent, Amine-binding Strips Immobilization of SEK1-CT on covalent, amine-binding strips was also accomplished in a stepwise procedure: the polymer was immobilized on a covalent, amine-binding plate first (1 hour), then treated with SMCC (1 hour). Conjugation of SEK1-CT to the immobilized polylysine was achieved simultaneously with the phosphorylation by ERK1. The polymers used were polylysine of MW ~35,000 and poly(lys, ala) 1:1 copolymer of MW ~35,000. The assay mixture comprising 5 μL of SEK1-CT, 5 μL of ADB, 10 μL of ERK1 and 10 μL of γ-$^{32}$P-ATP was incubated at room temperature for 15 minutes. An aliquot (10 μL) was then spotted on a phosphocellulose plate to stop the reaction. The radioactivity on the plate was determined using a Trilux Microbeta liquid scintillation counter. The radioactivity remaining on the surface of the wells after the plate was washed with water and 1% phosphoric acid was determined using a Beckmann liquid scintillation counter. The results of four assays conducted simultaneously are shown in Table 9. These results indicate that both polylysine and poly(lys, ala) copolymer conjugated SEK1-CT were efficiently immobilized on covalent, amine-binding plates and yielded high signal after phosphorylation. Also, the immobilization of polymer-conjugated SEK1-CT on the surfaces enhanced its phosphorylation. The radioactivity observed for the unconjugated SEK1-CT may result from non-specific binding of the amine groups on SEK1-CT to the plate. This non-specific binding could be eliminated by using polylysine as the blocking agent.

TABLE 9

Phosphorylation activity of SEK-1CT immobilized on covalent, amine-binding strips.

| | Assay | | | |
|---|---|---|---|---|
| Components | 1 | 2 | 3 | 4 |
| SEK1-CT-SMCC-polylysine | + | − | − | − |
| SEK1-CT-SMCC-poly(lys,ala) | − | + | − | − |
| SEK1-CT | − | − | + | − |
| ERK1 | + | + | + | + |

TABLE 9-continued

Phosphorylation activity of SEK-1CT immobilized on covalent, amine-binding strips.

| Components | Assay | | | |
| --- | --- | --- | --- | --- |
| | 1 | 2 | 3 | 4 |
| $\gamma$-$^{32}$P-ATP | + | + | + | + |
| Radioactivity (cpm) | 15500 | 15047 | 7570 | 2907 |

Example 10

Immobilization of a Polylysine-conjugated Substrate on Covalent, Sulfhydryl-binding Plates

Immobilization of a polylysine-conjugated substrate on covalent, sulfhydryl-binding plates was accomplished by using DTT in the final step to block the excess active sites and introduce sulfhydryl grops into the substrate. The immobilization was performed following two procedures. In the first procedure, the reaction mixture containing 5 µL of polylysine-conjugated substrate, 10 µL of enzyme, 10 µL of ADB and 5 µL of $\gamma$-$^{32}$P-ATP was incubated at room temperature for 15 minutes, and then transferred to the covalent, sulfhydryl-binding plate for a further 45 minutes incubation. In the second procedure, the immobilization and the phosphorylation of the polylysine-conjugated substrate were carried out simultaneously for 1 hour. The final washing step was the same for both procedures, i.e., the plate was washed sequentially with water, 1% phosphoric acid solution, water and ethanol. The radioactivity in each well was determined using a Trilux Microbeta liquid scintillation counter. Two polylysine-conjugated substrates, SEK1-CT-SMCC-polylysine and CAPK-sub-GMBS-polylysine, were prepared and immobilized on covalent, sulfhydryl-binding plates. The phosphorylation of these immobilized substrates was accomplished by CDK1, PAK and PIM, and the results are summarized in Table 10. All three substrates yielded high signals and the background was less than 500 cpm. Both immobilization procedures yielded consistent results.

TABLE 10

Phosphorylation activity of substrates immobilized on covalent, sulfhydryl-binding plates.

| Kinase/Substrate | Radioactivity (cpm) |
| --- | --- |
| CDK1/SEK1-CT-SMCC-polylysine | 11920 |
| PAK/CAPK-sub-GMBS-polylysine | 24140 |
| PIM/CAPK-sub-GMBS-polylysine | 29570 |
| ERK1/SEK1-CT-SMCC-polylysine | 47000[a] |

[a] simultaneous immobilization and phosphorylation by ERK1.

Example 11

Immobilization of a Polylysine-conjugated Substrate on Non-covalent Plates

The immobilization of polymer conjugated substrates on non-covalent plates was carried out simultaneously with phosphorylation. Enzyme assays on these non-specific binding plates were performed by sequentially adding the conjugated substrate, ADB, and the enzyme at 0° C., then $\gamma$-$^{32}$P-ATP to complete the phosphorylation reaction at room temperature. The results are summarized in Tables 11 and 12.

TABLE 11

Phosphorylation activity of substrate immobilized on different plates.

| | Radioactivity (cpm) | | |
| --- | --- | --- | --- |
| | Covalent, amine-binding | | Non-covalent |
| Substrate/Kinase | Opaque[a] | Transparent[b] | Medium Binding[b] |
| CAPK-sub-SMCC-polylysine/PIM | 9793 | 12873 | 4641 |
| SEK1-CT-SMCC-polylysine/CDK1 | 8955 | 7304 | 4021 |
| CAPK-sub-SMCC-polylysine/PAK | 28899 | 20965 | 16453 |

[a] Data obtained by a Beckmann LS 6500 counter;
[b] Data obtained by a Trilux 1450 counter.
Assay conditions: 5 µL of substrate, 10 µL of enzyme, 20 µL of ADB, 5 µL of hot ATP, and incubated at room temperature for 60 minutes.

TABLE 12

Phosphorylation activity of immobilized CAPK-sub-SMCC-polylysine on different non-covalent plates.

| | Radioactivity (cpm) | |
| --- | --- | --- |
| Non-Covalent Plate Type | Immobilized Plate[b] | Spotted Solution[a] |
| Hydrophobic-ionic easy wash | 8989 | 43028 |
| Hydrophobic-ionic U-bottom | 9019 | 46220 |
| Medium Binding[a] U-bottom | 5484 | 45464 |

NOTES:
The substrate was phosphorylated by PIM.
[a] Data obtained by a Trilux 1450 counter;
[b] Data obtained by a Beckmann LS 6500 counter.
Assay conditions: 5 µL of substrate, 20 µL of ADB, 10 µL of enzyme, 5 µL of hot ATP, and incubated at room temperature for 60 minutes.

Example 12

Optimization of Substrate Immobilization and Phosphorylation

Effect of incubation time. Incubation time is an important parameter during the high throughput inhibitor screening. High signal-to-noise ratio and the efficient use of robot time are desired. Normally, a prolonged reaction time would produce higher signal output from the immobilized plate and this effect is clearly shown by the data listed in Table 13. The results were obtained from the immobilized polylysine-conjugated CAPK-sub on a covalent, sulfhydryl-binding plate phosphorylated by PIM.

TABLE 13

Phosphorylation activity of immobilized CAPK-sub-GMBS-polylysine after phosphorylation by PIM.

| Incubation time (min) | Radioactivity (cpm) |
| --- | --- |
| 15 | 6530 |
| 60 | 24370 |

Effect of enzyme concentration. In general a higher signal output will be obtained if more enzyme is used for the phosphorylation. Two polylysine-conjugated substrates were immobilized on covalent, sulfhydryl-binding plates according to the second procedure described in Example 10 and phosphorylation was accomplished by CDK1 at room temperature for 60 minutes. The results are summarized in Table 14. A non-linear increase in phosphorylation with enzyme concentration was observed. One-fold increase in enzyme concentration afforded a 50% increase in activity.

TABLE 14

Effect of amount of CDK1 on the phosphorylation activity of different substrates.

| CDK | SEK1-CT-SMCC-polylysine | | CAPK-sub-SMCC-polylysine | |
|---|---|---|---|---|
| (µL) | On plate | In solution | On plate | In solution |
| 10 | 10186 | 9857 | 5800 | 18246 |
| 20 | 14545 | 15490 | 7727 | 35367 |

Effect of purification of the conjugated peptide. After the conjugation of peptide to the maleimide-functionalized polylysine, small molecules, such as the unconjugated peptide and excess blocking agent, are present in the reaction solution which can compete with the active sites on the plate. An additional purification step to remove small molecules may be performed before immobilization. The purification was carried out by gel filtration through a Sephadex® G-50F NICK Column. The comparative results of immobilizing purified and unpurified CAPK-sub-GMBS-polylysine samples to covalent, sulfhydryl-binding plates are summarized in Table 15. Higher activity was observed for the purified sample. This observation indicates some degree of competitive binding to the maleimide groups on the surface from the excess DTT present in the unpurified sample.

TABLE 15

Phosphorylation activity of immobilized CAPK-sub-GMBS-polylysine.

| | Radioactivity (cpm) | |
|---|---|---|
| Enzyme | Purified | Unpurified |
| PIM | 29570 | 18950 |
| PAK | 24140 | 21190 |

Effect of pH. In the case of immobilization to covalent, amine-binding plates, the pH effect was investigated. The immobilization of a conjugated-substrate to an covalent, amine-binding plate was achieved by incubating 100 µL of PBS buffer solution containing 10 µg of the conjugated-substrate at room temperature for an hour. The radioactivity of the immobilized plates is shown in Table 16. There was an increase in activity as the pH increased, however, the increase in activity was minimal.

TABLE 16

The effect of pH on phosphorylation activity.

| pH | SEK1-CT-GMBS-polylysine with ERK1 | CAPK-sub-SMCC-polylysine with PIM |
|---|---|---|
| 7 | 13300 | 4400 |
| 8 | 16050 | 5820 |
| 9 | 18065 | 6180 |

Example 13

Comparison of One-plate Assay and Two-plate Assay Methods

The one-plate assay was compared with the two-plate assay under the normal conditions employed by the high throughput screening robotic system: a mixture of 5 µL substrate (5 µg), 10 82 L enzyme, 10 µL ADB and 5 µL $\gamma$-$^{32}$P ATP was incubated at room temperature for 20 minutes. In the one-plate assay, a non-covalent, medium binding plate was used. The results are summarized in Table 17. These results demonstrate that the one-plate assay method affords a signal-to-noise ratio approximately 4–8 times higher than the two-plate assay method.

TABLE 17

Comparison of one-plate and two-plate assay methods.

| | Radioactivity (cpm) | | | | | | S/N ratio | |
|---|---|---|---|---|---|---|---|---|
| | PKB-sub/PKB | | | SEK1-CT/ERK1 | | | PKB- | SEK1- |
| Assay | Free | Conj | -ve control | Free | Conj | -ve control | sub | CT |
| One-plate | — | 48300 | 600 | — | 41000 | 350 | 81 | 117 |
| Two-plate | 38000 | — | 1700 | 2800 | — | 170 | 22 | 16 |

Example 14

Preparation of Functionally Modified Beads for Affinity Chromatography

The substrates can be any free peptide molecule or its polymer conjugate. Polylysine-conjugated CAPK-sub and CAPK-sub-GMBS-polylysine are used to demonstrate the procedure for the preparation of functionally modified beads for affinity chromatography.

A suspension of AffiGel 10 (4.5 mL) was place in a 14 mL sterile culture tube (Falcon). The solvent was removed by centrifugation. The sediment beads were then washed with 10 mL ice-cold water. The drained beads were obtained in a volume of about 2 mL. The washed beads were mixed with polylysine-conjugated CAPK-sub solution (2.5 mL), which was freshly prepared from 4 mg CAPK-sub following the procedure in Example 1.

The reaction mixture, in a total volume of about 4.7 mL, was rotary shaken at 4° C. for one hour, 5 mL water was added to the mixture, and the mixture was shaken at 4° C. overnight. 2-Aminoethanol (100 µmole) was added to block the remaining active sites on the beads. After incubation for one hour at room temperature, the mixture was centrifuged and 8.5 mL of the supernatant was removed for determination of substrate loading on the beads. The functionally modified beads were washed three times with 10 mL Tris-HCl buffer (0.1 M, pH 8) in 0.5 M NaCl and 10 mL acetate buffer (0.1 M, pH 4) in 0.5 M NaCl, and twice with 10 mL PBS buffer (pH 7.4). The washed beads were stored at 6° C. in PBS with 0.1% $NaN_3$. The substitution of CAPK-sub on the beads was estimated to be ~1 mg/mL AffiGel (~0.89 μmole/mL) by assaying the solution removed from the beads with PAK.

A standard CAPK-sub conjugate sample was used as the reference. Briefly, a phosphorylation of the standard CAPK-sub conjugate ($1.49 \times 10^{-3}$ μmole) by PAK produced a radioactivity of 81400 cpm. In the same assay of PAK, a phosphorylation of 8 μL mother-liquor produced 91542 cpm, which corresponds to $1.68 \times 10^{-3}$ μmole of the CAPK-sub conjugate in solution. Thus, in 8.5 mL mother-liquor solution there should be equivalent to 1.78 μmole or 1.99 mg of unconjugated CAPK-sub in solution. Therefore, the CAPK-sub conjugate immobilized on 2 mL beads should be (4.0–1.99)~2 mg CAPK-sub equivalent.

Example 15

Use of Affinity Columns to Enrich Phosphoproteins from Whole Cell Lysates or Organ Cytosol One mL of functionally modified beads was placed into a 1 cm column by gravity. Approximately 25 mg of rat liver cytosol or whole cell lysate was applied to the resin by passing the protein solution through the beads. The beads were washed with 10 column volumes of KTr-A. The column was then eluted with KTr-B, with the eluate collected in 1 mL fractions. The peak of protein elution was determined through Bradford protein assay. Binding percentage of the affinity resin was defined as follows:

[(Protein bound)/(Protein loaded)]×100%

Western blotting. 10 μg of affinity purified material was run on an 11% SDS-polyacrylamide gel, and transferred to nitrocellulose. Membranes were Western blotted using standard protocols, testing for the presence of known protein kinases. Efficiency of binding was determined through comparison of the amount of protein bound to the amount of protein remaining in the flow-through material from the column.

In vitro labeling. 100–200 μg of affinity purified material was incubated with 10 mM magnesium chloride, 1 mM manganese chloride, 25 μM ATP, 50 μCi $\gamma$-$^{32}$P-ATP at 30° C. for 30–60 minutes. The reaction was terminated through ethanol precipitation. The resulting proteins were analyzed by 2D electrophoresis according to standard protocols, using Pharmacia 18 cm 3–10 linear IPG (immobilized pH gradient) strips. The second dimensions were run using 20 cm×20 cm 11% duracryl gels. Proteins were visualized by silver staining, and phosphoproteins visualized using a Bio-Rad GS-525 molecular imager.

The subject methods provide a means to assay phosphorylation substrates and inhibitors that results in more efficient phosphorylation and an enhanced signal. The substrate is covalently linked to a polymer that increases the substrate availability and increases the sensitivity of detection of phosphorylation. The subject methods are an improvement over the existing methods for screening large numbers of agents which modulate the activity of phosphorylation enzymes. The bound substrate also provides for improved efficiency in the affinity purification of phosphorylation enzymes based on their binding to substrate.

What is claimed is:

1. An improved method for screening samples to perform a phosphorylation assay, wherein the sensitivity of said assay is improved relative to an unconjugated peptide substrate by the method comprising:

conjugating a peptide substrate to a signal enhancing polymer;

immobilizing said polymer and conjugated peptide substrate on a solid surface;

exposing said immobilized substrate to a mixture comprising a candidate modulating agent for phosphorylation; a phosphorylation enzyme, and detectably labeled source of phosphate groups, for a period of time sufficient for said enzyme to act on said substrate, and measuring the degree of phosphorylation of the substrate.

2. The method of claim 1 wherein said phosphorylation enzyme is a phosphatase.

3. The method of claim 1 wherein said phosphorylation enzyme is a protein kinase.

4. The method of claim 3, wherein said protein kinase is a serine/threonine kinase.

5. The method of claim 1, wherein said peptide substrates are conjugated to a polymer and immobilized on a solid surface in a single step.

6. The method of claim 1, wherein said peptide substrates are conjugated to said signal enhancing polymer via a bifunctional linker.

7. The method of claim 1, wherein said candidate modulating agent for phosphorylation is an inhibitor of phosphorylation.

8. The method of claim 1 wherein said candidate modulating agent for phosphorylation is an enhancer of phosphorylation.

9. The method of claim 1, wherein the polymer is a polyamine.

10. The method of claim 9, wherein the polyamine is polylysine.

11. The method of claim 10, wherein said polylysine polymer is from 400 to 500,000 Daltons in weight.

12. The method of claim 10, wherein said polylysine polymer is from 30,000 to 250,000 Daltons in weight.

13. The method of claim 1, wherein said solid surface comprises a multiwell plate.

14. The method of claim 1, wherein the solid surface is a microsphere.

15. The method of claim 6, wherein said bifunctional linker comprises a succinimidyl ester and a maleimide or iodoacetamide.

16. An improved method for affinity purification of phosphorylation enzymes, wherein the sensitivity is improved by the method comprising:

conjugating a peptide substrate to a signal enhancing polymer;

immobilizing said polymer and conjugated peptide substrate on a matrix;

exposing said immobilized substrate to a complex mixture comprising a candidate phosphorylation enzyme and detectably labeled source of phosphate groups; for a period of time sufficient for said enzyme to bind to said substrate;

washing said matrix free of unbound material; and eluting said candidate phosphorylation enzyme from said matrix.

17. The method of claim 16 wherein said phosphorylation enzyme is a phosphatase.

18. The method of claim 16 wherein said phosphorylation enzyme is a protein kinase.

19. The method of claim 18, wherein said protein kinase is a serine/threonine kinase.

20. The method of claim 16, wherein said peptide substrates are conjugated to said signal enhancing polymer via a bifunctional linker.

21. The method of claim 16, wherein the polymer is a polyamine.

22. The method of claim 21, wherein the polyamine is polylysine.

23. The method of claim 21, wherein said polylysine polymer is from 400 to 500,000 Daltons in weight.

24. The method of claim 21, wherein said polylysine polymer is from 30,000 to 250,000 Daltons in weight.

25. The method of claim 20, wherein said bifunctional linker comprises a succinimidyl ester and a maleimide or iodoacetamide.

* * * * *